US006863945B2

(12) United States Patent
Beitz et al.

(10) Patent No.: US 6,863,945 B2
(45) Date of Patent: Mar. 8, 2005

(54) USABLE SPLICE FOR A STABILIZED ABSORBENT

(75) Inventors: Mark J. Beitz, Appleton, WI (US); Alissa R. Bruss, Appleton, WI (US); Robert J. Makolin, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 98 days.

(21) Appl. No.: 10/039,238

(22) Filed: Dec. 31, 2001

(65) Prior Publication Data

US 2003/0125686 A1 Jul. 3, 2003

(51) Int. Cl.[7] ................................................ B32B 3/00
(52) U.S. Cl. .............................. 428/61; 428/57; 428/58
(58) Field of Search .............................. 428/57, 58, 61

(56) References Cited

U.S. PATENT DOCUMENTS

| | | | |
|---|---|---|---|
| 2,495,761 A | 1/1950 | Platt | |
| 2,737,466 A | 3/1956 | Utermohlen, Jr., et al. | |
| 3,633,352 A | 1/1972 | Marriner | |
| 3,886,031 A | 5/1975 | Taitel | |
| 4,190,483 A | 2/1980 | Ryan et al. | |
| 4,303,712 A | * 12/1981 | Woodroof | 428/58 |
| 4,374,576 A | 2/1983 | Ryan | |
| 4,776,920 A | 10/1988 | Ryan | |
| 4,798,603 A | 1/1989 | Meyer et al. | |
| 4,923,546 A | 5/1990 | Wheeler et al. | |
| 5,176,668 A | 1/1993 | Bernardin | |
| 5,176,672 A | 1/1993 | Bruemmer et al. | |
| 5,192,606 A | 3/1993 | Proxmire et al. | |
| 5,509,915 A | 4/1996 | Hanson et al. | |
| 5,514,237 A | 5/1996 | Emenaker et al. | |
| 5,584,897 A | 12/1996 | Christianson et al. | |
| 5,750,217 A | 5/1998 | Kearby et al. | |
| 6,160,197 A | 12/2000 | Lassen et al. | |

FOREIGN PATENT DOCUMENTS

| | | |
|---|---|---|
| DE | 19602575 A1 | 7/1997 |
| EP | 0842756 A1 | 5/1998 |
| EP | 0844062 A1 | 5/1998 |
| WO | WO 99/59907 | 11/1999 |
| WO | WO 00/77286 A1 | 12/2000 |
| WO | WO 02/102665 A1 | 12/2002 |

* cited by examiner

Primary Examiner—Elizabeth M. Cole
Assistant Examiner—Norca L. Torres
(74) Attorney, Agent, or Firm—Senniger Powers

(57) ABSTRACT

A process for splicing a first portion of absorbent material to a second portion of absorbent material to form a longer, continuous length of absorbent material suitable for uninterrupted sequential infeed to a processing machine. The process includes the steps of placing a trailing end of the first portion adjacent a leading end of the second portion and aligning the ends. A piece of splicing material is attached to the ends. The piece of splicing material has a fluid permeability at least about as great as a fluid permeability of the first portion of absorbent material and at least about as great as a fluid permeability of the second portion of absorbent material. In other aspects, the disclosure includes a spliced, continuous length of absorbent material, and a personal care absorbent article formed from the spliced absorbent material.

14 Claims, 6 Drawing Sheets

USABLE SPLICE FOR A STABILIZED ABSORBENT

BACKGROUND OF THE INVENTION

This invention generally relates to the manufacture of absorbent articles from absorbent material, and in particular to a splice connecting two portions of absorbent material which is useable in articles.

Personal care absorbent articles such as disposable diapers, training pants, other infant care products, other child care products, feminine napkins, panty liners, interlabial pads, other feminine care products, incontinence articles, and other adult care products are typically manufactured using high-speed processing machines which convert a stabilized web or ribbon of a fibrous absorbent material into an article. Each web is pre-formed and provided to the machine as a wound roll or coil. To prevent interruption of the processing machine a trailing end of each coil is spliced to a leading end of the next coil. The resulting interconnected web has sufficient tensile strength so that it may be provided to the machine and processed without breaking at the splice.

One drawback to conventional splicing techniques is that the splice is not fluid permeable and therefore unusable in an article. In the past, fibrous absorbent materials have been joined by an adhesive or, since they do not have smooth surfaces which readily hold an adhesive, by an adhesive tape. Adhesives and tape are substantially impermeable to fluid. They hinder fluid from being absorbed by the absorbent structure of the article and degrade effectiveness of the article. As a result, it is necessary to cull all spliced regions of the absorbent material, or to cull all articles having a portion of a spliced region, in order to remove all adhesive or tape. In practice, as many as seven articles are culled per splice, producing a costly loss in efficiency and waste of material.

SUMMARY OF THE INVENTION

In general, a process according to the present invention splices a first portion of absorbent material to a second portion of absorbent material to form a longer, continuous length of absorbent material suitable for uninterrupted sequential infeed to a processing machine. The process comprises the steps of placing a trailing end of the first portion adjacent a leading end of the second portion, and aligning the trailing end of the first portion with the leading end of the second portion. A piece of splicing material is attached to the trailing end of the first portion and the leading end of the second portion. The piece of splicing material has a fluid permeability at least about as great as a fluid permeability of the first portion of absorbent material and at least about as great as a fluid permeability of the second portion of absorbent material.

In another aspect, the present invention comprises a continuous length of absorbent material for uninterrupted sequential infeed to a processing machine. The length includes a first portion of absorbent material having a trailing end and a second portion of absorbent material having a leading end adjacent to and aligned with the trailing end of the first portion of absorbent material. A piece of splicing material is attached to the trailing end of the first portion and to the leading end of the second portion of absorbent material. The splicing material has a fluid permeability at least about as great as a fluid permeability of the first portion of absorbent material and at least about as great as the second portion of absorbent material.

In yet a further aspect, a personal care absorbent article according to the present invention has a spliced absorbent material. The article comprises a fluid permeable body side liner for placement adjacent a wearer. An absorbent core is attached to the body side liner for absorbing fluid passing through the liner. The absorbent core includes a first portion of absorbent material, a second portion of absorbent material, and a piece of splicing material directly attached to the first and second portions of absorbent material. The splicing material has a fluid permeability at least about as great as a fluid permeability of the first portion of absorbent material and at least about as great as the second portion of absorbent material.

In still a further aspect, a process according to the present invention splices a first portion of absorbent material to a second portion of absorbent material to form a longer, continuous length of absorbent material suitable for uninterrupted sequential infeed to a processing machine. The process comprises the steps of placing a trailing end of the first portion adjacent a leading end of the second portion, and aligning the trailing end of the first portion with the leading end of the second portion. A piece of splicing material is attached to the trailing end of the first portion and the leading end of the second portion. The piece of splicing material has a fluid permeability at least about 25% as great as a fluid permeability of the first portion of absorbent material and at least about 25% as great as a fluid permeability of the second portion of absorbent material.

Other features of the present invention will be in part apparent and in part pointed out hereinafter.

BRIEF DESCRIPTION OF THE DRAWINGS

Corresponding reference characters indicate corresponding parts throughout the views of the drawings.

DETAILED DESCRIPTION

Figure 1A:
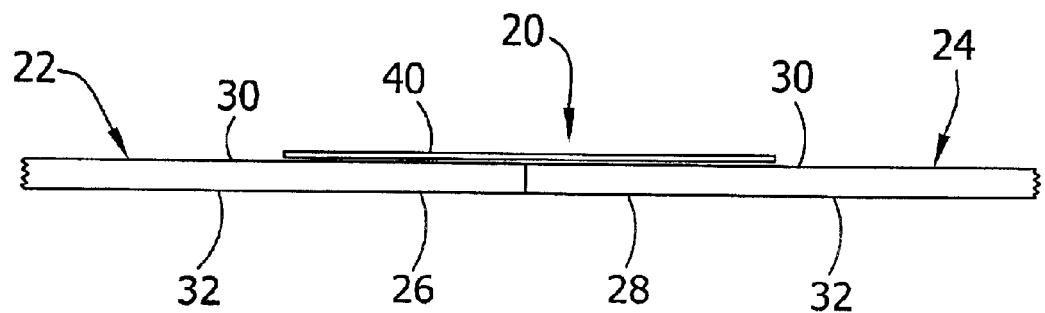
FIG. 1A is a fragmentary schematic elevation of a continuous length of absorbent material of a first embodiment of the present invention.
Figure 1B:
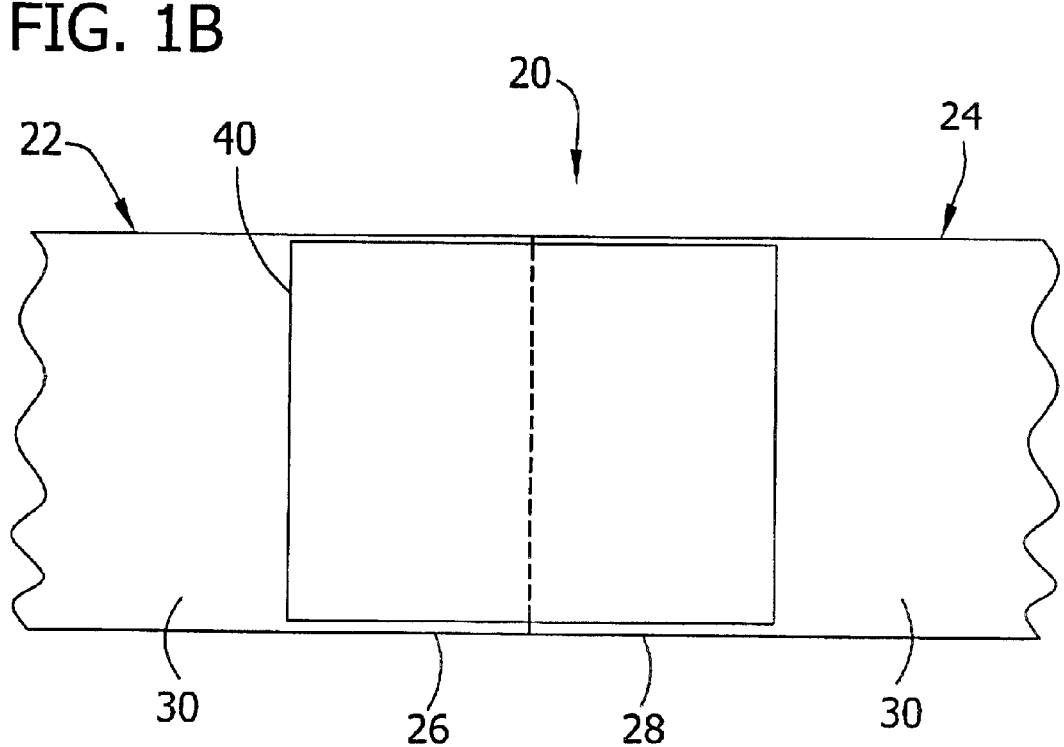
FIG. 1B is a schematic plan of the length of absorbent material shown in FIG. 1A.

Referring now to the drawings and in particular to FIGS. 1A and 1B, a continuous length of absorbent material is indicated generally at 20. The length of material 20 generally includes first and second portions of absorbent material, generally designated 22 and 24, respectively, which are serially supplied to a processing machine (not shown) for converting the absorbent material into absorbent articles.

During manufacture of the absorbent articles, the continuous length of absorbent material 20 is introduced into the processing machine from a suitable supply. For example, the absorbent material may be delivered from a series of supply rolls or coils (not shown), or may optionally be supplied from an upstream inline manufacturing operation. The use of successive coils requires that first and second portions 22, 24, which are typically from different coils, be spliced together to form a continuous length to avoid disrupting machine operation.

The length of material 20 made according to the present invention is useable in absorbent articles, including, but not limited to, disposable diapers, training pants, other infant care products, other child care products, feminine napkins, panty liners, interlabial pads, other feminine care products, incontinence articles, and other adult care products. Typically, the articles are disposable and not intended for washing and reuse. An exemplary article which may include the length of material described herein is disclosed in U.S. Pat. No. 6,160,197 issued Dec. 12, 2000, to Lassen et al. and entitled "Absorbent Article Having A Body-Accommodating Absorbent Core", which is hereby incorporated by reference. Briefly, the Lassen reference discloses a feminine hygiene product and more particularly a sanitary napkin having a liquid-previous cover or body side liner, a liquid-impervious baffle or outer cover positioned opposite the body side liner, and an absorbent core positioned between the body side liner and the outer cover.

Examples of diaper configurations suitable for use in connection with the instant application are described in U.S. Pat. No. 4,798,603 issued Jan. 17, 1989, in the name of Meyer et al. and entitled "ABSORBENT ARTICLE HAVING A HYDROPHOBIC TRANSPORT LAYER"; U.S. Pat. No. 5,176,668 issued Jan. 5, 1993, in the name of Bernardin and entitled "ABSORBENT STRUCTURE DESIGNED FOR ABSORBING BODY FLUIDS"; U.S. Pat. No. 5,176,672 issued Jan. 5, 1993, in the name of Bruemmer et al. and entitled "POCKET-LIKE DIAPER OR ABSORBENT ARTICLE"; U.S. Pat. No. 5,192,606 issued Mar. 9, 1993, in the name of Proxmire et al. and entitled "ABSORBENT ARTICLE HAVING A LINER WHICH EXHIBITS IMPROVED SOFTNESS AND DRYNESS, AND PROVIDES FOR RAPID UPTAKE OF LIQUID", and U.S. Pat. No. 5,509,915 issued Apr. 23, 1996 in the name of Hanson et al. and entitled "THIN ABSORBENT ARTICLE HAVING RAPID UPTAKE OF LIQUID", the disclosures of which are hereby incorporated by reference.

The first portion of absorbent material 22 has a trailing end 26. The second portion of absorbent material 24 has a leading end 28. Typically, the first and second portions 22, 24 are identical in all respects but they may be different without departing from the scope of the present invention. For example, the second portion 24 may have a different material composition than the first portion 22.

The trailing end 26 of the first portion is placed adjacent the leading end 28 of the second portion, and the ends are laterally and vertically aligned as shown in FIGS. 1A and 1B. In the illustrated embodiment, the ends 26, 28 are placed squarely end-to-end as for a conventional butt joint. The ends may be in engagement, or may be spaced apart by a small gap between the ends. The placing of the ends 26, 28 at these positions may be done manually, or by automated machine. An end-to-end arrangement results in better product comfort than an arrangement with the ends overlapped because it is thinner and less bulky. Each of the portions 22, 24 has a first face 30 and an opposite second face 32. The respective first faces 30 of the first and second portions 22, 24 are oriented in an identical direction (e.g., vertically upward, as shown in the drawings). Similarly, the respective second faces 32 are oriented in an identical direction (e.g., vertically downward). It is understood that the faces 30, 32 may be oriented in non-identical directions without departing from the scope of this invention.

A piece of splicing material 40 is positioned adjacent the trailing end 26 of the first portion 22 and the leading end 28 of the second portion 24 for attachment thereto. The piece of splicing material 40 engages at least one of the faces 30, 32 of each of the ends. For the arrangement shown in FIGS. 1A and 1B, the piece of splicing material 40 is positioned adjacent the first face 30 of the trailing end 26 of the first portion and the first face 30 of the leading end 28 of the second portion.

The relative sizes of the materials may vary. Desirably, the piece of splicing material 40 is slightly narrower than the first and second portions 22, 24 of absorbent material so that it does not extend beyond the lateral sides of the material, but yet covers a sufficient shear area to produce an effectively strong splice. A typical airlaid absorbent material for a personal care absorbent article, such as each of the portions 22, 24, is about 2 to 10 mm thick and between about 30 and 150 mm wide. The piece of splicing material 40 should overlap each portion of absorbent material in the longitudinal direction by a length sufficient to form a strong splice. For example, the portions 22, 24 of an absorbent material having a width of about 37 mm may be suitably joined by splicing material 40 having a longitudinal overlap of at least about 25 mm per end (producing a total length of splice of about 50 mm), and more desirably a longitudinal overlap of at least about 50 mm. Additional overlap beyond 50 mm would also offer additional splice strength if it would be necessary for material processing.

In one embodiment, the piece of splicing material 40 is attached to the respective ends 26, 28 of the first and second portions of absorbent material 22, 24 by compressing the arrangement and applying heat energy. The attachment is made using a conventional compression device (not shown), such as a press, anvil, or set of plates which are pressed together. The heat may originate from either a surface source (such as a heated compression device) or from a hot air source such as a through-air bonding technique. The applications of heat and pressure occur simultaneously for a period of time so that the splicing material and/or a binding agent of the absorbent material soften or begin to melt and bind together upon cooling. As these techniques are conventional and well understood by those of ordinary skill in the art, they will not be discussed in further detail.

Alternatively, the addition of an adhesive may be used to supplement attachment of the splicing material to the absorbent material via heat and compression. Examples of suitable adhesives include but are not limited to hot melt adhesives, pressure sensitive adhesives, and latex adhesives. The adhesive may be applied via methods which include but are not limited to melt spray, bead spray, rotogravure, and spreader rod.

Significantly, the piece of splicing material 40 is at least about 25% as fluid permeable as the first and second portions 22, 24 of absorbent materials. More optimally, the splicing material 40 is about as fluid permeable as the first and second portions 22, 24 of absorbent materials. Therefore, the splice will not hinder passage of fluid to the absorbent material when incorporated into an article. Further, the splicing material 40 has a tensile strength sufficient so that the splice is strong and will not rupture when processed into an absorbent article. More optimally, the splicing material has a tensile strength at least as great as a tensile strength of the absorbent material so that the splice is strong and will not rupture when processed into an absorbent article.

The first and second portions 22, 24 of absorbent material may include cellulosic fibers (e.g., wood pulp fibers), other natural fibers, synthetic fibers, superabsorbent material in the form of particles or fibers, binder materials, surfactants, selected hydrophobic materials, or the like, polyester fiber, bicomponent fiber, latex, as well as combinations thereof, and other materials suitable to improve absorbent performance and/or web processing. Desirably, the stabilized absorbent material has between about 2% and about 50% polymer content by weight.

Stabilized absorbent is typically a material capable of retaining fluid to a saturated capacity of at least about 3 g/g and about 10 g of fluid per 0.1 square meter of material as measured by a 0.5 psi saturated capacity test method. Further, the material holds together when dry or at any level of fluid saturation. Dry tensile properties of the material is typically in the range of 0.1–60 kg per cm of material width. Example materials may include an airlaid absorbent bonded with thermally bondable fibers. An example of thermally bondable fibers is CELBOND T-255 fiber manufactured by KoSa Corporation, having offices in Charlotte, N.C. Another example of thermally bondable fibers is ES fiber manufactured by ES Fibervisions, having offices in Athens, Ga. Alternatively, the airlaid absorbent may be bonded with dried latex or a binding powder. An example binding powder is VINNEX, available from Wacker Polymer Systems L.P. having offices in Adrian, Mich. Alternatively, the absorbent material may be bonded by hydrogen bonding or in a wetlaid process.

The absorbent materials are typically formed by employing conventional airlaying techniques, as known in the art. Other techniques are also employed to form stabilized absorbent webs. Such techniques include: dry-forming techniques, wet-laying techniques, foam-forming techniques, and various wet-forming techniques. The resulting absorbent webs have included absorbent fibers, natural fibers, synthetic fibers, superabsorbent materials, binders, and strengthening components in desired combinations. The stabilized webs may be employed to generate preformed absorbent sheets or layers, and the preformed material may be stored in a preformed supply, such as provided by a supply roll. At an appropriate time, the preformed layer may be delivered from the preformed supply into a manufacturing line.

Suitable stabilized absorbents containing superabsorbent powders for urine absorbing applications typically have a basis weight in the range of about 200–1500 gsm and a web density of about 0.05–0.35 $g/cm^3$. Suitable stabilized airlaid absorbents not containing superabsorbent powders for feminine hygiene or other applications typically have a basis weight in the range of about 100–500 gsm and a web density of about 0.05–0.25 $g/cm^3$. The low density and high basis weight of these materials cause lower than desired roll lengths, forcing the need for a more than desirable number of splices.

Desirably, the splicing material of the piece 40 is melt compatible with the binder fiber of the absorbent material. One type of splicing material is a carded web comprising bicomponent fibers used to stabilize absorbent structures. These bicomponent fibers may be comprised of a fiber with a core of polyester and a sheath of polyethylene. An example bicomponent fiber of this type is CELBOND T-255 fiber manufactured by KoSa Corporation. Alternatively, bicomponent fibers may be comprised of a polypropylene core and a sheath of polyethylene. An example fiber of this type is ES fiber, manufactured by ES Fibervisions. Other polyolefins may be used as splicing material. Desirably, the splicing material has a very permeable, open structure.

An alternative splicing material 40 would be a carded web comprised of a blend of bicomponent and one or more additional types of staple fibers. Examples of the staple fibers include but are not limited to polyethylene in fibers, polypropylene fibers, and polyester fibers.

Another alternative splicing material 40 is a nonwoven material made via a process other than carded web technology. Examples include but are not limited to spunbonded fabrics, spunlaced fabrics, meltblown fabrics, spunbond-meltblown-spunbond (SMS) fabrics, spunbond-meltblown-meltblown-spunbond (SMMS) fabrics, bicomponent fluid distribution layer (BFDL) or other nonwoven material functioning as a liquid surge management layer in a personal care product, laminates of two or more materials in intimate association, hydroentangled nonwovens, scrim, needlepunched nonwoven material, perforated films, and other nonwoven material comprised in part of a polymer compatible with the synthetic binding material providing stability to the absorbent material to be spliced.

Another alternative splicing material 40 is a woven fabric comprised in part of a polymer compatible with the synthetic binding material providing stability to the absorbent material to be spliced.

The fibers in the splicing material 40 may also be treated with a finish to enhance fluid handling properties. A surfactant may be added during the manufacturing of the staple fiber, filament, thread, or yarn. Alternatively, a surfactant may be added to the woven or nonwoven material within the process of manufacturing the woven or nonwoven material.

Alternatively, the fibers of the splicing material 40 may be adhesively covered to assist the thermal bonding to the portions 22, 24 of stabilized absorbent material. The covering of adhesive may fully encapsulate some or all of the fibers of the splicing material 40, and may be on only a portion of the fibers of the splicing material. The covering of adhesive may be spread evenly across a surface of the piece of splicing material, or may be spread in a pattern over the surface. Examples include but are not limited to dot patterns, straight line patterns, curvilinear line patterns. Ideally, the covering of adhesive does not impede the fluid handling properties of the spliced material while still providing additional bonding strength for the splice.

The splicing material 40 should not impede fluid intake. Accordingly, the splicing material is at least about 25%, and more desirably more than 100%, as fluid permeable as the portions 22, 24 of absorbent material(s) being spliced together. Further, it is desirable for the continuous length 20 (with the splicing material attached) to be about as permeable as absorbent material without the splicing material attached.

The splicing material is sufficiently strong and has sufficient tensile strength to be processed through the processing machine. Preferably, the splice material has a tensile strength at least as great as a tensile strength of the absorbent material.

Figure 2A:
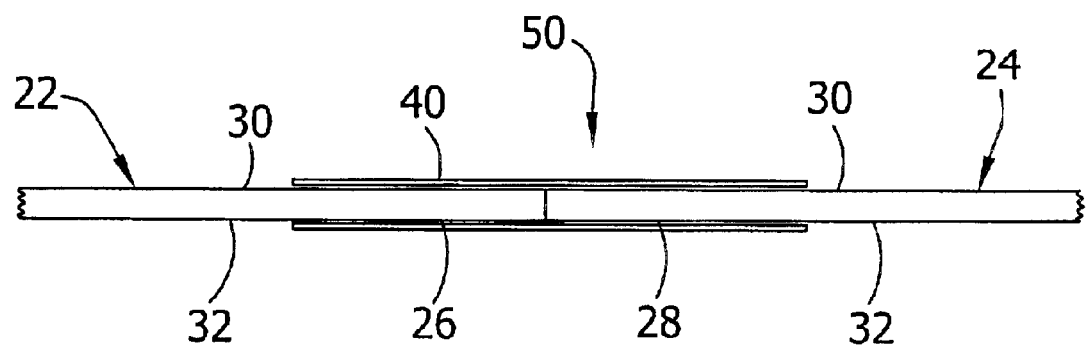
FIGS. 2A and 2B are a schematic elevation and plan, respectively, of a length of absorbent material of a second embodiment.
Figure 2B:
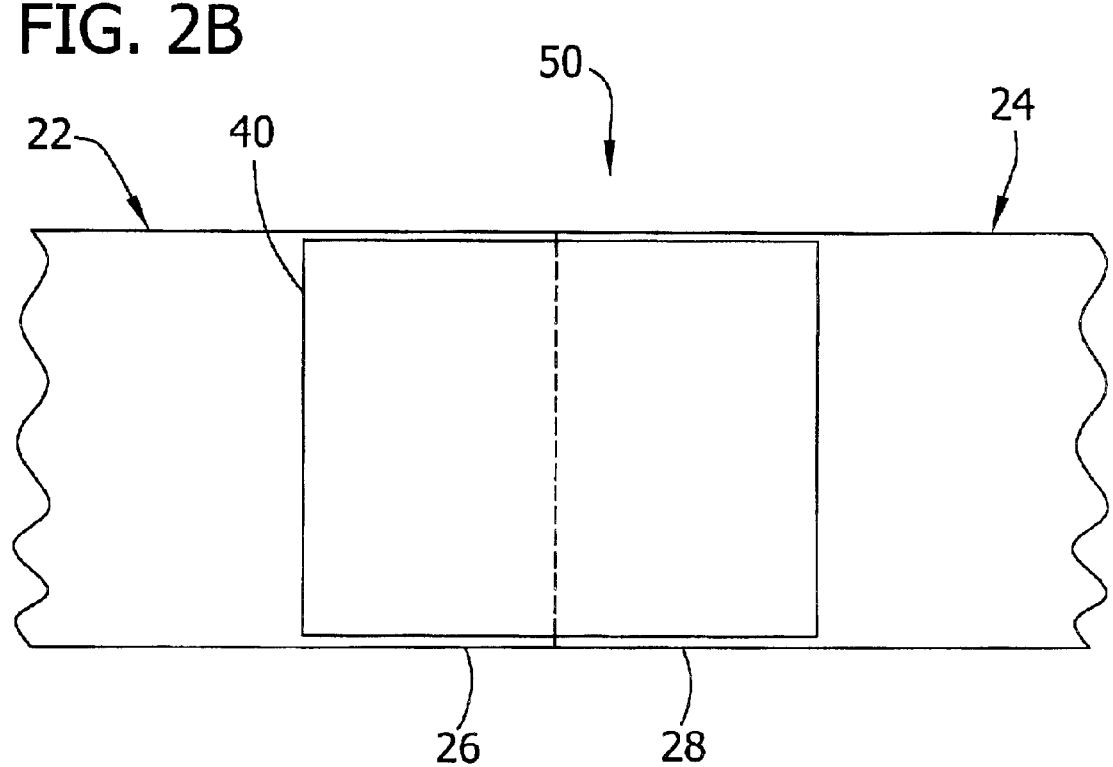

A second embodiment of a continuous length of absorbent material 50 includes two pieces of splicing material 40 on opposite faces of the ends is shown in FIGS. 2A and 2B. A second piece of splicing material 40 is placed on the second face 32 of the trailing end 26 of the first portion of absorbent material 22 and the second face 32 of the leading end 28 of the second portion of absorbent material 24. The second embodiment has the advantage of a stronger splice because in provides more shear area and more cross-sectional area of splice material. Alternatively, the second embodiment may permit use of splicing material pieces having narrower widths without reducing the strength of the splice.

Figure 3A:
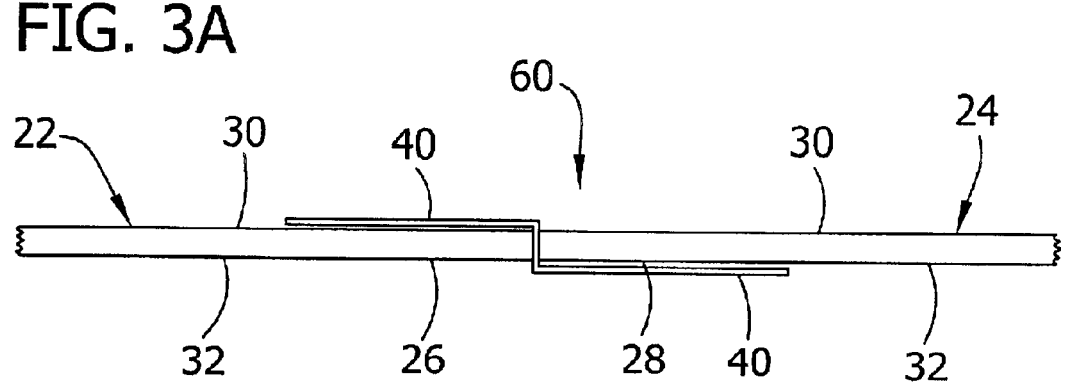
FIGS. 3A and 3B are views similar to FIGS. 1A and 1B of a third embodiment of the present invention.
Figure 3B:
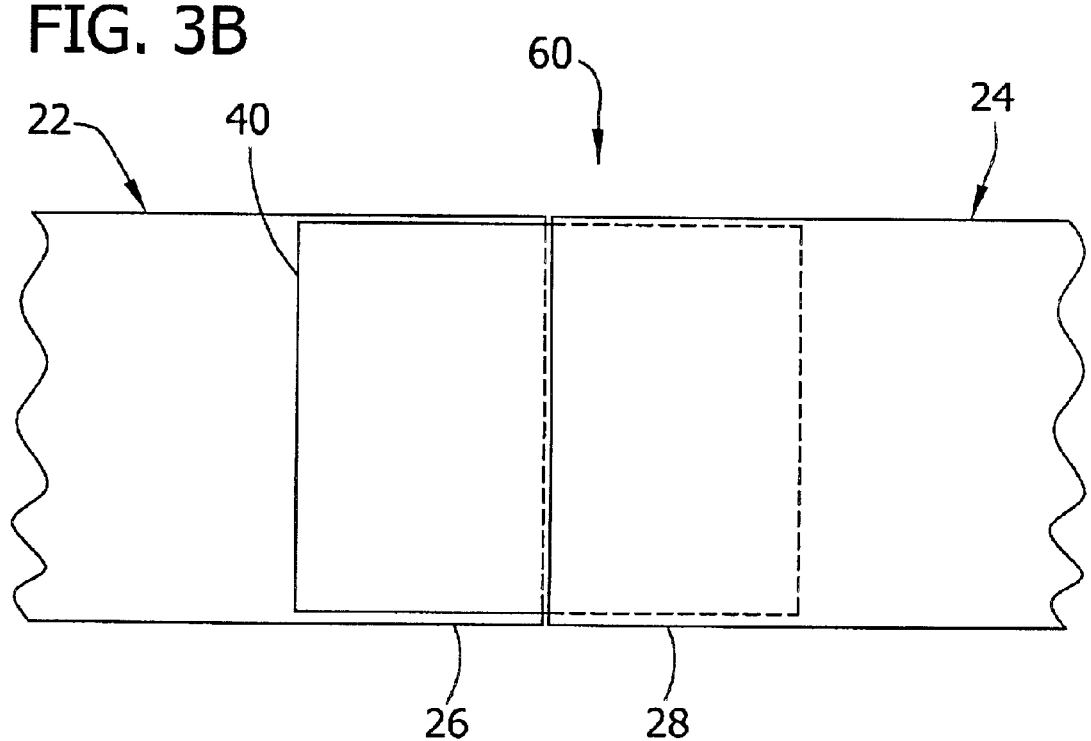

A third embodiment of a continuous length of absorbent material 60, shown in FIGS. 3A and 3B, places a single piece of splicing material 40 on the first face 30 of the trailing end 26 of the first portion 22 and the second face 32 of the leading end 28 of the second portion 24.

Figure 4A:
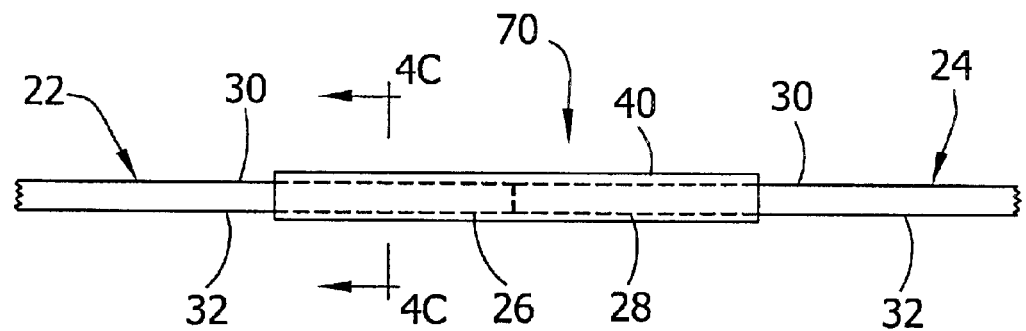
FIGS. 4A and 4B are views similar to FIGS. 1A and 1B of a fourth embodiment of the present invention.
Figure 4B:
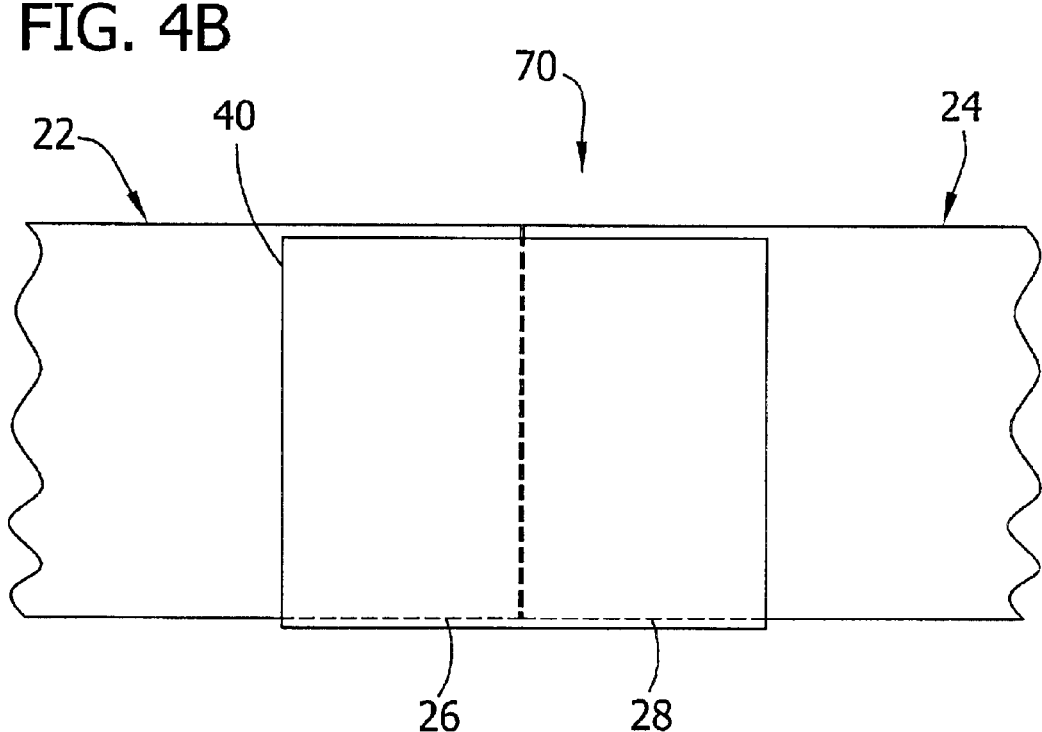
Figure 4C:
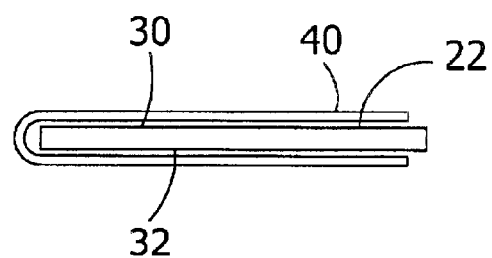
FIG. 4C is a view taken on line 4C—4C of FIG. 4A.

A fourth embodiment of a continuous length of absorbent material 70, shown in FIGS. 4A, 4B, and 4C, wraps the piece of splicing material 40 around both faces 30, 32 of the ends 26, 28.

Figure 5A:
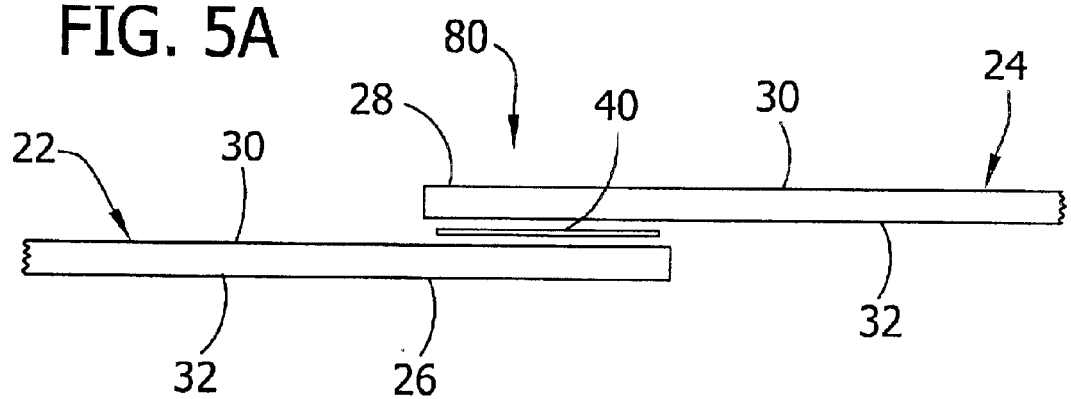
FIGS. 5A and 5B are views similar to FIGS. 1A and 1B of a fifth embodiment of the present invention.
Figure 5B:
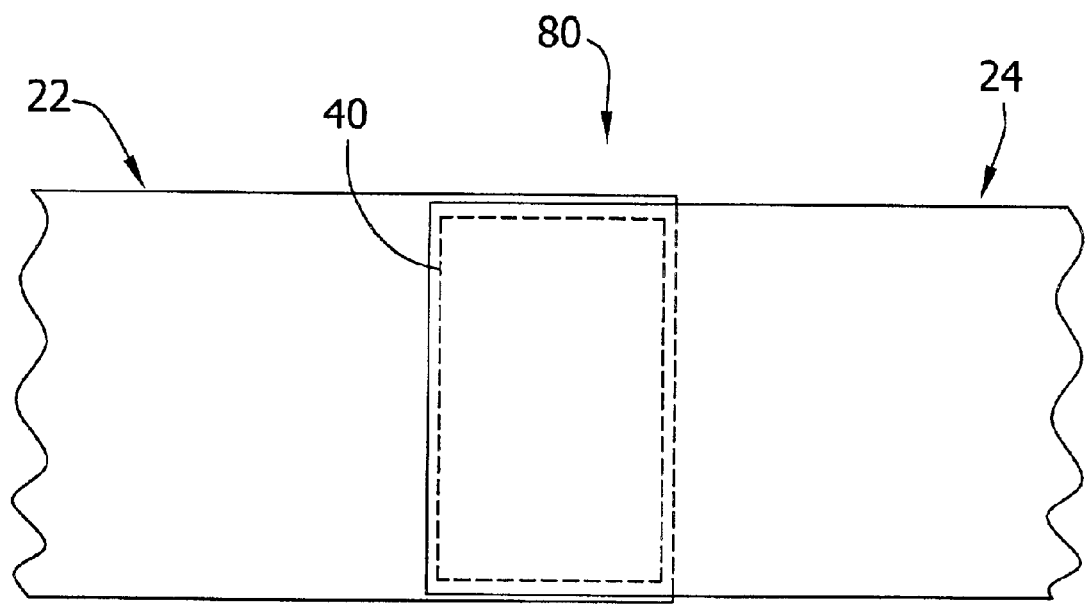

A fifth embodiment of a continuous length of absorbent material 80, shown in FIGS. 5A and 5B, places the piece of splicing material 40 in a sandwiched position between overlapping ends 26, 28 of the first portion 22 and the second portion 24.

It is understood that other arrangements may be used without departing from the scope of this invention. An adhesive tape may be used in combination with any of these arrangements to further strengthen the splice. However, if such tape is used, the manufactured articles containing that tape will possibly need to be culled.

Each end 26, 28 of the portions of absorbent material 22, 24 is shown with generally square, right angles and the piece of splicing material 40 is shown as having a rectangular shape. However, the portions of absorbent material 22, 24 and piece(s) of splicing material 40 may have other shapes and angles without departing from the scope of this invention. Specifically, the ends 26, 28 of the portions of absorbent material may be angled or irregularly shaped, and pieces of splicing material 40 may have an irregular shape or a shape which does not match the shape of the ends. Further, the two ends 26, 28 of the portions of absorbent material need not have corresponding shapes. Gaps between ends 26, 28 may be large and spanned by the piece of splicing material 40.

The present invention is illustrated by the following example which is merely for the purpose of illustration and is not to be regarded as limiting the scope of the invention or the manner in which it is practiced.

EXAMPLE 1

A thermally bonded airlaid absorbent comprised of about 50% superabsorbent polymer, about 45% fluff pulp and about 5% of KoSa T-255 Merge 35100A sample is cut to a specimen size of about 102×102 mm. A sample of through air bonded carded web (TABCW) material comprised of 100% Chisso ESC-HR6 material and having basis weight of about 17 gsm is also cut to a specimen size of about 102×102 mm and then placed directly on top of the airlaid sample. The sample is wrapped in a paper towel (HI-DRI, sold commercially by Kimberly-Clark Corporation). The sample is then pressed at about 500 kg using a Carver press for about six seconds at a temperature of about 135 C. The paper towel overwrap is then removed. The sample is then placed between two plates of a conventional fluid intake test apparatus having a column above the plates for depositing fluid. The side with the splice material attached faces the open hold and column on the top plate of the apparatus.

COMPARATIVE EXAMPLE 2

The same thermally bonded airlaid absorbent used in Example 1 comprised of about 50% superabsorbent polymer, about 45% fluff pulp, and about 5% of KoSa T-255 Merge 35100A sample is cut to a specimen size of about 102×102 mm. There is no splice or splice material for Example 2.

A measurement of permeability is done by using a fluid intake test method as follows: 1) Weigh the sample on an electronic balance to 0.01 g accuracy. 2) Measure the thickness of sample to a 0.01 mm accuracy using 0.2 psi of pressure using a Miutoyo IDF-1050E with a brass platen or equivalent bulk measuring apparatus. 3) Place a 4 inch by 4 inch specimen centered on the 4.5×4.5" base of the fluid intake test apparatus. 4) Place the top board through the pins on the bottom board and over the specimen to be tested. 5) Measure out approximate ⅓ of the 0.9% saline (Ricca Chemical Co. #7210-2.5) required to fully saturate the specimen as measured by a $3.4 \times 10^3$ Pa retention capacity test. For the 600 gsm specimen, this was found to be about 35.0+/−0.1 g of 0.9% saline. 6) Pour the saline through the hole in the sample. Measure the amount of time taken between the time saline hits the sample and all of the saline to enter the sample using a stopwatch with 0.01 second accuracy. 7) Wait 15 minutes. 8) Repeat steps 5 and 6 for a second insult. 9) Wait 15 minutes. 10) Repeat steps 5 and 6 for a third insult. 11) Remove the sample from the board. 12) Weight a paper towel (HI-DRI, sold commercially by Kimberly-Clark Corporation). 13) Wrap the wet sample with the paper towel. The paper towel is used to contain any absorbent material which may escape during the soaking process. 14) Soak the sample in 0.9% saline for 20 minutes. 15) Soak an preweighed paper towel in the saline for 20 minutes to determine its saturated capacity. 16) Desorb any excess saline from the specimen and the paper towel blank using a $3.4 \times 10^3$ Pa retention capacity tester (KC item #1551369 or equivalent) for 5 minutes. 17) Weigh the specimen and the wet paper towel. 18) Determine the wet pick-up of the saturated sample through the formulas:

g/g capacity of towel=(wet weight towel−dry weight towel)/dry weight towel

Wet pick-up sample=Wet weight measured−Dry weight sample−(1+g/g capacity of towel)*weight of towel 19) Determine the percent saturation at each insult from the amount insulted at that point and the wet pick-up of the sample. 20) Determine the intake rate is cc/sec through dividing the intake in seconds into the insult size. 21) Plot intake rate versus percent saturation.

Comparison of the measure of permeability is defined as comparing the second intake rate with the splice material on top of the sample to the second intake rate without the splice material on top of the sample. Alternatively, the comparison of the measure of permeability is defined as comparing the second intake rate with the splice material on top of the sample to the second intake rate without the splice material on top of the sample.

Figure 6:
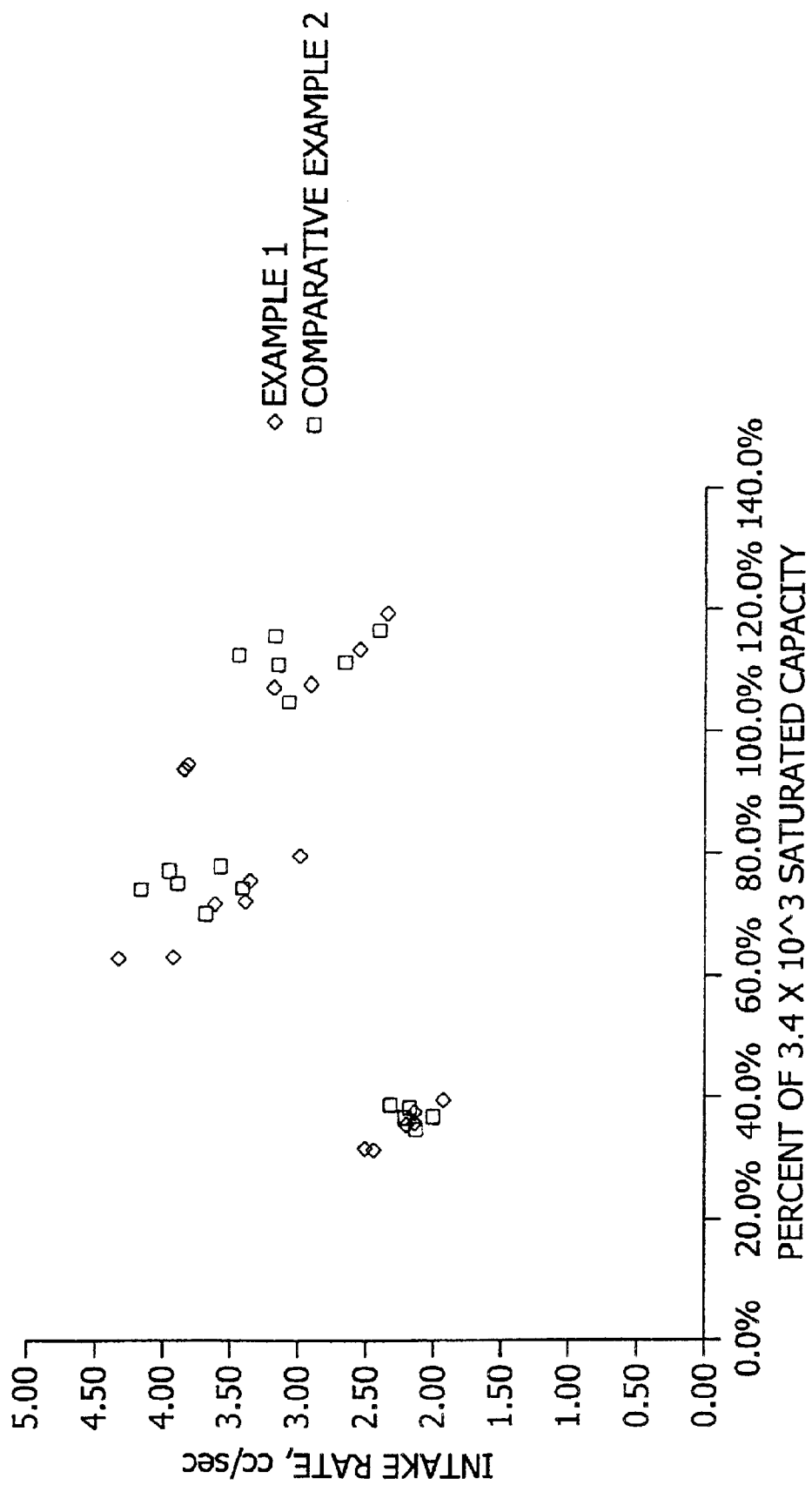
FIG. 6 is a plot of measured fluid intake rate versus percent saturation in 0.9% saline for a representative example of the invention.

FIG. 6 is a plot of the fluid intake rate versus the saturations. Example 1, the material with the splice material attached to the top surface of the airlaid, has essentially equal 0.9% saline intake rate to Comparative Example 2, the airlaid material without splice material attached to the top surface.

Tensile strength of splices made from materials shown in Example 1 with the configuration shown in FIGS. 1A and 1B is typically between 0.45 kg and 2.25 kg per cm of material width, although splices having strengths outside these bounds do not depart from the scope of the present invention. The tensile strength of the splice can be increased or decreased by changing the adhesion of the splicing material on the absorbent material, or by changing the contact area of the splicing material on the absorbent material, or by changing the tensile strength of the splicing material. Any combination of these changes may also be used to increase or decrease the tensile strength of the splice.

Thus the present invention provides a splice which is strong, dry or wet, and which facilitates a fluid intake equal to that of non-spliced absorbent material. Accordingly, manufactured articles which incorporate the splice need not be culled.

Although various illustrative and representative configurations have been described in detail herein, it is to be appreciated that other variants, modifications and arrangements are possible. All of such variations, modifications and arrangements are to be considered as being within the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. A continuous length of absorbent material for uninterrupted sequential infeed to a processing machine, comprising:
   a first portion of absorbent material having a trailing end;
   a second portion of absorbent material having a leading end adjacent to and aligned with the trailing end of the first portion of absorbent material thereby defining an aligned junction of the first and second portions having a length extending generally transverse of the first and second portions; the first portion of absorbent material and the second portion of absorbent material each having a length sufficient to form a plurality of absorbent articles;
   a piece of splicing material attached to both of said trailing end of said first portion and to said leading end of said second portion of absorbent material such that the splicing material extends continuously over a majority of the length of the aligned junction, said splicing material including fibers having polyolefin content and having a fluid permeability at least about 25% as great as a fluid permeability of said first portion of absorbent material and at least about 25% as great as said second portion of absorbent material.

2. A continuous length of absorbent material as set forth in claim 1 wherein said splicing material has a fluid permeability at least about as great as a fluid permeability of said first portion of absorbent material and at least about as great as said second portion of absorbent material.

3. A continuous length of absorbent material as set forth in claim 2 wherein said piece of splicing material is thermally bonded to said trailing end of said first portion and to said leading end of said second portion.

4. A continuous length of absorbent material as said forth in claim 3 wherein said piece of splicing material comprises a carded web of bicomponent fibers.

5. A continuous length of absorbent material as set forth in claim 1 wherein said first and second portions of absorbent material each include fibers having polyolefin in content.

6. A continuous length of absorbent material as set forth in claim 1 wherein said piece of splicing material is thermally bonding to said first and second portions of absorbent material.

7. A continuous length of absorbent material as set forth in claim 1 wherein said splicing material is a carded web comprising bicomponent fibers.

8. A continuous length of absorbent material as set forth in claim 1 wherein the trailing end of said first portion is arranged squarely end-to-end adjacent the leading end of said second portion.

9. A continuous length of absorbent material as set forth in claim 1 wherein said trailing end of said first portion overlaps the leading end of said second portion.

10. A continuous length of absorbent material as set forth in claim 1 wherein each of said ends of the first and second portions of absorbent material has a first major surface and an opposite second major surface, and wherein the piece of splicing material comprises is attached to at least one of said first and second major surfaces of each of said ends.

11. A continuous length of absorbent material as set forth in claim 10 wherein the first surface of the trailing end of the first portion and the first surface of the leading end of the second portion are oriented in an identical direction, and wherein said piece of splicing material is attached to the first surface of the trailing end of the first portion and to the first surface of the leading end of the second portion.

12. A continuous length of absorbent material as set forth in claim 11 wherein said piece of splicing material is a first piece of splicing material attached to said first surface of the trailing end of the first portion and to said first surface of the leading end of the second portion, further comprising a second piece of splicing material attached to the second surface of the trailing end of the first portion and to the second surface of the leading end of the second portion.

13. A continuous length of absorbent material as set fort in claim 10 wherein the first surface of the trailing end of the first portion and the first surf ace of the leading end of the second portion are oriented in an identical direction, and wherein said piece of splicing material is attached to the first surface of the end of the first portion and to the second surface of the end of the second portion.

14. A continuous length of absorbent material as set forth in claim 10 wherein the piece of splicing material is wrapped around both of said surfaces of each of said ends.

* * * * *

UNITED STATES PATENT AND TRADEMARK OFFICE
CERTIFICATE OF CORRECTION

PATENT NO. : 6,863,945 B2
DATED : March 8, 2005
INVENTOR(S) : Mark J. Beitz et al.

It is certified that error appears in the above-identified patent and that said Letters Patent is hereby corrected as shown below:

<u>Column 6,</u>
Line 4, "Polyethylene in fibers" should read -- polyethylene fibers --

Signed and Sealed this

Fifth Day of July, 2005

JON W. DUDAS
*Director of the United States Patent and Trademark Office*